United States Patent
Wakimoto et al.

(10) Patent No.: US 8,110,601 B2
(45) Date of Patent: Feb. 7, 2012

(54) COMPOUND, $\alpha_1$ ADRENERGIC RECEPTOR ANTAGONISTIC AGENT, AND COMPOSITION

(75) Inventors: Toshiyuki Wakimoto, Shizuoka (JP); Haruo Nukaya, Shizuoka (JP); Yoshihide Suwa, Ashiya (JP); Yoshiaki Yokoo, Fuchu (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 334 days.

(21) Appl. No.: 12/522,776

(22) PCT Filed: Jan. 22, 2008

(86) PCT No.: PCT/JP2008/050747
§ 371 (c)(1),
(2), (4) Date: Sep. 24, 2009

(87) PCT Pub. No.: WO2008/090857
PCT Pub. Date: Jul. 31, 2008

(65) Prior Publication Data
US 2010/0004328 A1 Jan. 7, 2010

(30) Foreign Application Priority Data
Jan. 22, 2007 (JP) .................. 2007-012019

(51) Int. Cl.
*A61K 31/343* (2006.01)
*C07D 307/80* (2006.01)
(52) U.S. Cl. ....................... 514/469; 549/467
(58) Field of Classification Search .............. 514/469; 549/467
See application file for complete search history.

(56) References Cited

FOREIGN PATENT DOCUMENTS

| | | |
|---|---|---|
| JP | 2004/002978 | 1/2004 |
| JP | 2006/057406 | 6/2006 |
| JP | 2006/092893 | 9/2006 |
| JP | 2006-273842 | 10/2006 |

OTHER PUBLICATIONS

Yueh-Hsiung Kuo et al., "Synthesis of 5-(3-Hydroxypropyl)-7-methoxy-2-(3'-methoxy-4'-hydroxyphenyl)-3-benzo[b]Furancarbaldehyde, a Novel Adenosine $A_1$ Receptor Ligand from the Root of Salvia Miltiorrhiza" J. Nat. Prod., 1996, pp. 625-628, vol. 59, No. 6.
Joel G. Hardman et al., "Goodman & Gilman's The Pharmacological Basis of Therapeutics", The McGraw-Hill Companies, $10^{th}$ Edition, 2001, pp. 241-249.
International Search Report mailed Feb. 19, 2008 in International PCT Application PCT/JP2008/050747 filed Jan. 22, 2008.
International Preliminary Report on Patentability (PCT/IB/373) issued Jul. 28, 2009 for International PCT Application PCT/JP2008/050747 filed Jan. 22, 2008.
Written Opinion (PCT/ISA/237) for International PCT Application PCT/JP2008/050747 filed Jan. 22, 2008.

*Primary Examiner* — Taofiq A Solola
(74) *Attorney, Agent, or Firm* — Drinker Biddle & Reath LLP (57) ABSTRACT

A novel compound, a novel $\alpha_1$ adrenergic receptor antagonistic agent, and a novel composition are provided which are capable of exerting a therapeutic effect on treatment of hypertension as well as treatment of prostatic hypertrophy and the like. The compound is represented by the following formula (1):

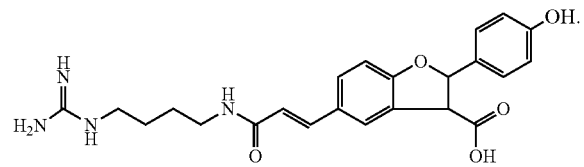

6 Claims, 2 Drawing Sheets

COMPOUND, $\alpha_1$ ADRENERGIC RECEPTOR ANTAGONISTIC AGENT, AND COMPOSITION

CROSS REFERENCE TO RELATED APPLICATIONS:

This application is the National Stage of International Application No. PCT/JP2008/050747, filed Jan. 22, 2008, and claims benefit of Japanese Application No. 2007-012019, filed Jan. 22, 2007, both of which are herein incorporated by reference in their entirety.

TECHNICAL FIELD

The present invention relates to a compound capable of acting on an $\alpha_1$ adrenergic receptor.

BACKGROUND ART

An autonomic nervous system is formed of a sympathetic nervous system and a parasympathetic nervous system, and involuntarily controls actions of internal organs, blood vessels and the like.

For example, when an impulse is transmitted through the sympathetic nerve to a cardiovascular system (such as heart and blood vessels), a blood pressure, pulse and the like are adjusted by increasing a heart rate and constricting the blood vessels. In this case, in the sympathetic nerve, a substance (neurotransmitter) called adrenaline or noradrenaline is secreted from a terminal (synapse) of a nerve cell. These neurotransmitter act on specific receptors present in the heart or vascular smooth muscles, by which impulses are transmitted to the heart and blood vessels, to thereby control the actions thereof.

Herein, the receptor on which adrenaline and noradrenaline can act is called an adrenergic receptor, and classified into two types: $\alpha$ receptor and $\beta$ receptor. The $\alpha$ receptor is further classified into $\alpha_1$ receptor and $\alpha_2$ receptor, while the $\beta$ receptor is further classified into $\beta_1$ receptor and $\beta_2$ receptor.

Briefly, the $\alpha$ receptor is associated with functions including vasoconstriction, and the $\beta$ receptor is associated with functions including increase in the heart rate. It should be noted that the $\alpha_1$ adrenergic receptor is known to be present in the vascular smooth muscle, prostatic smooth muscle and the like, and is associated with constrictions thereof.

An antagonist of the adrenergic receptor is capable of acting on the above-mentioned $\alpha$ receptor or $\beta$ receptor competitively or noncompetitively with the neurotransmitters (such as adrenaline and noradrenaline), to block a transmission of an impulse by the neurotransmitter in the sympathetic nerve.

Therefore, for example, when the antagonist capable of acting on the $\alpha_1$ adrenergic receptor (hereinafter, referred to as "$\alpha_1$ adrenergic receptor antagonist") acts on the $\alpha_1$ adrenergic receptor present in the vascular smooth muscle, it is possible to make the vascular smooth muscle relaxed to dilate the blood vessel. As a result, a vascular resistance is reduced which in turn reduces the blood pressure (in other words, the antagonist is capable of functioning as a hypotensive drug).

Examples of the conventional $\alpha_1$ adrenergic receptor antagonist having such a function include phentolamine, phenoxybenzamine and prazosin, and an $\alpha_1$ adrenergic receptor antagonistic agent including these $\alpha_1$ adrenergic receptor antagonists has been used mainly as an antihypertensive drug, or as a drug for prostatic hypertrophy or the like (see nonpatent document 1). It should be noted that the prostatic hypertrophy is characterized as a benign tumor of a prostate grand with a high prevalence in elderly men, which is likely to become a factor of dysuria. The $\alpha_1$ adrenergic receptor antagonist may release the constriction of a urethra caused by prostatic hypertrophy and thus improve urination, by acting on the $\alpha_1$ adrenergic receptor present in the prostatic smooth muscle.

However, the conventional $\alpha_1$ adrenergic receptor antagonistic agents are often accompanied by various side effects (e.g., orthostatic hypotension and vertigo), and thus it has been desired that a novel $\alpha_1$ adrenergic receptor antagonistic agent be further developed.

The present invention is made with the view toward solving the above-mentioned current conditions, and provides a novel compound, an $\alpha_1$ adrenergic receptor antagonistic agent and a composition, which are capable of exerting a therapeutic effect in treatment of hypertension as well as treatment of prostatic hypertrophy and the like.

Nonpatent Document 1: "Goodman & Gilman's The Pharmacological Basis of Therapeutics 10th edition" (Vol. 1), translation supervised by Shuuji Takaori, Hideomi Fukuda and Akinori Akaike, Hirokawa Book Co., p 308-316

DISCLOSURE OF THE INVENTION

A first aspect of the compound according to the present invention is that the compound is represented by the following formula (1):

[Action and Effect]

As will be shown in Experimental Examples 1 and 2 below, the intensive and extensive studies by the present inventors elucidated for the first time that the compound represented by the formula (1) has a high binding activity to the $\alpha_1$ adrenergic receptor as well as a vasoconstriction-inhibitory action.

In other words, the compound represented by the formula (1) has a function as the $\alpha_1$ adrenergic receptor antagonist to block the transmission of the impulse in the form of neurotransmitter (such as adrenaline and noradrenaline) in the sympathetic nerve, by acting on the $\alpha_1$ adrenergic receptor present in the vascular smooth muscle, prostatic smooth muscle or the like.

A second aspect of the compound according to the present invention is that the compound is represented by the following formula (2):

[Action and Effect]

As will be shown in Experimental Examples 1 and 2 below, the intensive and extensive studies by the present inventors elucidated for the first time that the compound represented by the formula (2) has a high binding activity to the $\alpha_1$ adrenergic receptor as well as a vasoconstriction-inhibitory action.

In other words, the compound represented by the formula (2) has a function as the $\alpha_1$ adrenergic receptor antagonist to block the transmission of the impulse in the form of neurotransmitter (such as adrenaline and noradrenaline) in the sympathetic nerve, by acting on the $\alpha_1$ adrenergic receptor present in the vascular smooth muscle, prostatic smooth muscle or the like.

A first aspect of the $\alpha_1$ adrenergic receptor antagonistic agent according to the present invention is that the agent includes a compound represented by the following formula (1) as an active ingredient:

[Action and Effect]

As will be shown in Experimental Examples 1 and 2 below, the intensive and extensive studies by the present inventors elucidated for the first time that the compound represented by the formula (1) has a high binding activity to the $\alpha_1$ adrenergic receptor as well as a vasoconstriction-inhibitory action.

In other words, the compound represented by the formula (1) has a function as the $\alpha_1$ adrenergic receptor antagonist to block the transmission of the impulse in the form of neurotransmitter (such as adrenaline and noradrenaline) in the sympathetic nerve, by acting on the $\alpha_1$ adrenergic receptor present in the vascular smooth muscle, prostatic smooth muscle or the like.

Therefore, the $\alpha_1$ adrenergic receptor antagonistic agent of the present invention including the compound represented by the formula (1) as an active ingredient can exert an excellent therapeutic effect for hypertension, prostatic hypertrophy and the like.

A second aspect of the $\alpha_1$ adrenergic receptor antagonistic agent according to the present invention is that the agent includes a compound represented by the following formula (2) as an active ingredient:

[Action and Effect]

As will be shown in Experimental Examples 1 and 2 below, the intensive and extensive studies by the present inventors elucidated for the first time that the compound represented by the formula (2) has a high binding activity to the $\alpha_1$ adrenergic receptor as well as a vasoconstriction-inhibitory action.

In other words, the compound represented by the formula (2) has a function as the $\alpha_1$ adrenergic receptor antagonist to block the transmission of the impulse in the form of neurotransmitter (such as adrenaline and noradrenaline) in the sympathetic nerve, by acting on the $\alpha_1$ adrenergic receptor present in the vascular smooth muscle, prostatic smooth muscle or the like.

Therefore, the $\alpha_1$ adrenergic receptor antagonistic agent of the present invention including the compound represented by the formula (2) as an active ingredient can exert an excellent therapeutic effect for hypertension, prostatic hypertrophy and the like.

A third aspect of the $\alpha_1$ adrenergic receptor antagonistic agent according to the present invention is that the agent is any one of an antihypertensive drug, a drug for prostatic hypertrophy, and a diuretic.

[Action and Effect]

The $\alpha_1$ adrenergic receptor antagonistic agent of the present invention can exert an excellent therapeutic effect for hypertension, prostatic hypertrophy, dysuria and the like.

A first aspect of the composition according to the present invention is that the composition includes a compound represented by the following formula (1) and has an action through an $\alpha_1$ adrenergic receptor:

[Action and Effect]

As will be shown in Experimental Examples 1 and 2 below, the intensive and extensive studies by the present inventors elucidated for the first time that the compound represented by the formula (1) has a high binding activity to the $\alpha_1$ adrenergic receptor as well as a vasoconstriction-inhibitory action.

In other words, the compound represented by the formula (1) has a function as the $\alpha_1$ adrenergic receptor antagonist to block the transmission of the impulse in the form of neurotransmitter (such as adrenaline and noradrenaline) in the sympathetic nerve, by acting on the $\alpha_1$ adrenergic receptor present in the vascular smooth muscle, prostatic smooth muscle or the like.

Therefore, the composition of the present invention including the compound represented by the formula (1) can exert an excellent therapeutic effect for hypertension, prostatic hypertrophy and the like through the action via the $\alpha_1$ adrenergic receptor.

A second aspect of the composition according to the present invention is that the composition includes a compound represented by the following formula (2) and has an action through an $\alpha_1$ adrenergic receptor:

[Action and Effect]

As will be shown in Experimental Examples 1 and 2 below, the intensive and extensive studies by the present inventors elucidated for the first time that the compound represented by the formula (2) has a high binding activity to the $\alpha_1$ adrenergic receptor as well as a vasoconstriction-inhibitory action.

In other words, the compound represented by the formula (2) has a function as the $\alpha_1$ adrenergic receptor antagonist to block the transmission of the impulse in the form of neurotransmitter (such as adrenaline and noradrenaline) in the sympathetic nerve, by acting on the $\alpha_1$ adrenergic receptor present in the vascular smooth muscle, prostatic smooth muscle or the like.

Therefore, the composition of the present invention including the compound represented by the formula (2) can exert an excellent therapeutic effect for hypertension, prostatic hypertrophy and the like through an action via the $\alpha_1$ adrenergic receptor.

A third aspect of the composition according to the present invention is that the composition is any one of food and beverage, food and beverage additive, and veterinary feedstuff.

[Action and Effect]

Since the composition of the present invention can be consumed as food and beverage, intake of one of the compound represented by the formula (1) and the compound represented by the formula (2) becomes facilitated.

In addition, the food and beverage can be provided as those manufactured by common production methods (such as common food (including health food) and food with health claims (food for specified health use or food with nutrient function claims)), and as compared with drugs and the like, they are easily distributed in the market, enhancing availability to consumers.

When the composition of the present invention is used as the food and beverage additive, the composition may be provided as those with various purposes (e.g., seasoning, seasoned liquid, aroma essence, Furikake condiment, edible oil, soup stock, and nutritional fortifier), and thus can be added to various food and beverage.

Accordingly, as compared with the case where there is a necessity to purchase specific food and beverage that contains one of the compound represented by the formula (1) and the compound represented by the formula (2), intake of these compounds through eating and drinking can be more facilitated.

In addition, the composition of the present invention can be fed to specific animals as veterinary feedstuff; for allowing the animal to easily consume one of the compound represented by the formula (1) and the compound represented by the formula (2).

A fourth aspect of the composition according to the present invention is that the composition is accompanied with an indication with respect to a function based on an action through the $\alpha_1$ adrenergic receptor.

[Action and Effect]

Since the composition of the present invention is accompanied with an indication with respect to a function based on an action through the $\alpha_1$ adrenergic receptor, the composition is easily recognized by consumers and provides safety.

BEST MODE FOR CARRYING OUT THE INVENTION

Embodiments of the present invention will be described below with reference to the drawings.

EMBODIMENT

1. Method for Synthesizing Compound of the Present Invention

Figure 1:
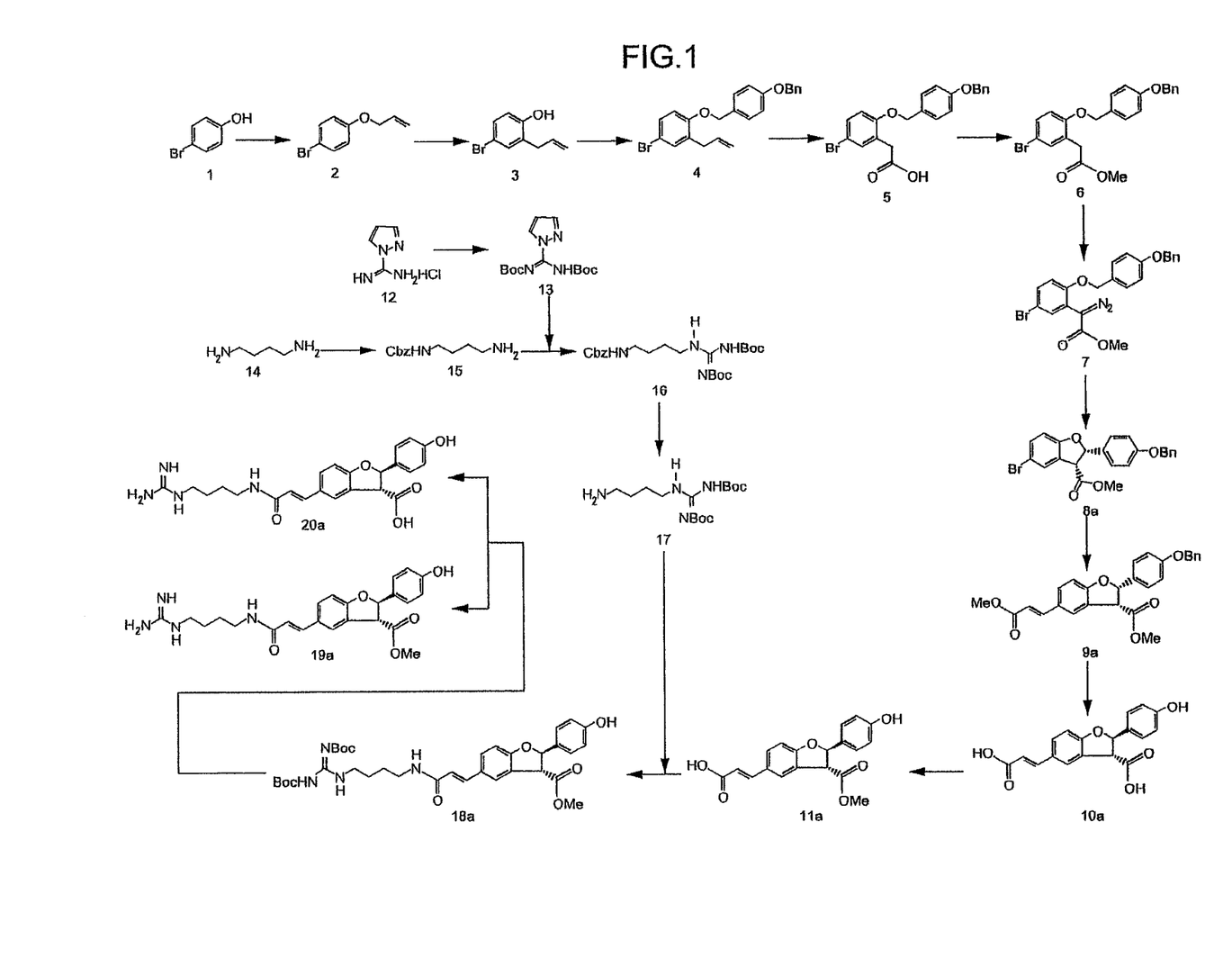
FIG. 1 is a diagram showing an entire synthesis scheme of the compound of the present invention.

FIG. 1 is a diagram showing an entire synthesis scheme of the compound of the present invention. Referential numerals (1 to 20a) indicate respective compounds. It should be noted that reagents and reaction conditions are not limited to those described below, and any kind of reagents and reaction conditions can be applied as long as the compounds are synthesized in accordance with the present synthesis scheme.

As shown in FIG. 1, the compounds 19a and 20a of the present invention can be synthesized by condensating a base moiety (compound 17) and an acyl moiety (compound 11a), which has been separately synthesized. Likewise, the compounds 19b and 20b of the present invention can be synthesized by condensating a base moiety (compound 17) and an acyl moiety (compound 11b), which has been separately synthesized.

(1) Synthesis of Base Moiety

With respect to the synthesis of a base moiety, first, N,N'-di-Boc-1H-pyrazole-1-carboxyamidine (compound 13) is synthesized from 1H-pyrazole-1-carboxyamidine hydrochloride (compound 12) in accordance with the method described in a literature (B. Drake et al., Synthesis, 579, 1994). Herein, the term "Boc" means t-butoxycarbonyl group ($-COOC(CH_3)_3$ group).

In addition, an amino group of 1,4-diaminobutane (compound 14), which is commercially available, is protected with a carbobenzoxy group (Cbz group), to thereby obtain 4-Cbz-aminobutyl-amine hydrochloride (compound 15) (A. Graham et al., Synthesis, 1032, 1984). By reacting the thus prepared compounds 13 and 15 in the presence of triethylamine, 4-carbobenzoxyamino-N,N'-di-Boc-agmatine (compound 16) is obtained.

The compound 16 is subjected to a hydrogenolysis reaction in a stream of hydrogen in the presence of 5% palladium carbon, to thereby obtain N,N'-di-Boc-agmatine (compound 17). For the compound 17, a hydrochloride thereof commercially available may be used.

(2) Synthesis of Acyl Moiety

For the synthesis of an acyl moiety, p-bromophenol (compound 1) and potassium carbonate ($K_2CO_3$) are stirred in dimethylformamide (DMF), and to the mixture is added allyl bromide, which is further stirred at room temperature. The reaction liquid is subjected to extraction using water and diethyl ether ($Et_2O$), and an aqueous phase is further subjected to extraction using diethyl ether. Two organic phases are combined and dried using magnesium sulfate ($MgSO_4$), and then subjected to filtration. The filtrate is concentrated under reduced pressure using an evaporator, to thereby obtain a pale yellow oily substance. The resultant oily substance is subjected to purification using silica gel chromatography, to thereby obtain 1-allyloxy-4-bromobenzene (compound 2) as a transparent and colorless oily substance.

Next, the compound 2 is heated in an oil bath at 200° C. The reaction liquid is subjected to extraction using water and diethyl ether, and an aqueous phase is further subjected to extraction using diethyl ether. Two organic phases are combined and dried using magnesium sulfate (MgSO$_4$), and then subjected to filtration. The filtrate is concentrated under reduced pressure using an evaporator, to thereby obtain a black oily substance. The resultant black oily substance is subjected to purification using silica gel chromatography, to thereby obtain 2-allyl-4-bromophenol (compound 3) as a pale yellow oily substance.

Next, the compound 3, potassium carbonate (K$_2$CO$_3$) and benzyloxy-benzylchloride (BnBr) are dissolved in dimethylformamide (DMF), and stirred at room temperature. The reaction liquid is subjected to extraction using water and ethyl acetate (AcOEt). The organic phase is washed with water, dried using magnesium sulfate (MgSO$_4$), and then subjected to filtration. The filtrate is concentrated under reduced pressure using an evaporator. The resultant residue is subjected to purification using silica gel chromatography, to thereby obtain 2-allyl-1-(4-benzyloxy-benzyloxy)-4-bromobenzene (compound 4).

Next, the compound 4, sodium periodate (NaIO$_4$) and ruthenium (III) chloride trihydrate (RuCl$_3$-3H$_2$O) are stirred in a mixed liquid of carbon tetrachloride (CCl$_4$)-acetonitrile (MeCN)-water for a predetermined time period, to which sodium periodate (NaIO$_4$) is added and the mixture is stirred for another several hours. The reaction liquid is subjected to extraction using water and chloroform (CHCl$_3$), and an aqueous phase is washed with chloroform (CHCl$_3$). Two organic phases are combined and dried using magnesium sulfate (MgSO$_4$), and then concentrated under reduced pressure using an evaporator. The resultant oily substance is subjected to purification using silica gel chromatography, to thereby obtain 2-(4-benzyloxy-benzyloxy)-5-bromophenylacetic acid (compound 5) as white solid.

Next, the compound 5 and diazomethane (CH$_2$N$_2$) prepared in an ether solution are stirred at room temperature, and after a predetermined time period, the solvent is volatilized. The resultant substance is subjected to purification using silica gel chromatography, to thereby obtain 2-(4-benzyloxy-benzyloxy)-5-bromophenylacetic acid methyl ester (compound 6) as white powder.

Next, the compound 6 and p-acetamidebenzenesulfonyl azide are stirred in acetonitrile (MeCN), during which 1,8-diazabicyclo[5.4.0]undec-7-ene (DBU) is added thereto. After a predetermined time period, to the mixture is added an aqueous solution of saturated ammonium chloride, and extraction is performed using diethyl ether and an aqueous solution of saturated ammonium chloride. The organic phase is washed with saturated saline, dried using magnesium sulfate (MgSO$_4$), and then subjected to filtration. The filtrate is concentrated under reduced pressure using an evaporator, to thereby obtain an oily substance. The resultant oily substance is subjected to purification to concentrate using silica gel chromatography, and further subjected to purification using spherical neutral silica gel chromatography, to thereby obtain 2-(4-benzyloxy-benzyloxy)-5-bromophenyl-diazo-acetic acid methyl ester (compound 7) as a yellow oily substance.

Next, the compound 7, optically-active dirhodium (II) complex (see H. Saito, et. al., Org. Lett. 4, 3887-3890 (2002); and W. Kurosawa, et. al., Tetrahedron 60, 9615-9628 (2004)), and a molecular sieve are added to distilled dichloromethane, and stirred at −78° C. for a predetermined time period. The reaction liquid is concentrated under reduced pressure using an evaporator. The residue is subjected to purification using silica gel chromatography, to thereby obtain 5-bromo-2-(4-benzyloxy)phenyl-3-methoxycarbonyl-2,3-di-hydrobenzofuran (compound 8a or 8b) as a white powdery substance.

In this case, when Tetrakis[N-phthaloyl-(R)-tert-leucinato]dirhodium bis(ethyl acetate) adduct (hereinafter, referred to as "Rh$_2$(R-PTTL)$_4$") is used as the optically-active dirhodium (II) complex, the following compound 8a is obtained.

Compound 8a

When Tetrakis[N-phthaloyl-(S)-tert-leucinato]dirhodium bis(ethyl acetate) adduct (hereinafter, referred to as "Rh$_2$(S-PTTL)$_4$") is used as the optically-active dirhodium (II) complex, the following compound 8b is obtained.

Compound 8b

It should be noted that, in FIG. 1, only the compound 8a is depicted for convenience sake.

Next, the compound 8a or 8b, methyl acrylate, tri(o-tolyl) phosphine, palladium acetate (Pd(OAc)$_2$), and distilled triethylamine (NEt$_3$) are reacted in dehydrated dimethylformamide (DMF) for a predetermined time period in a sealed container, which is in an oil bath at 100° C. After the reaction container is cooled, the reaction liquid is added to a predetermined amount of an aqueous solution of saturated ammonium chloride and a predetermined amount of ethyl acetate, which have been cooled to 0° C. in advance. Extraction is performed using an aqueous solution of saturated ammonium chloride and ethyl acetate, and the organic phase is washed with an aqueous solution of saturated ammonium chloride. The organic phase is dried using magnesium sulfate (MgSO$_4$), and then subjected to filtration. The filtrate is concentrated under reduced pressure using an evaporator, to thereby obtain an oily substance. The resultant oily substance is subjected to purification using silica gel chromatography, to thereby obtain 2-(4-benzyloxy)phenyl-5-trans(2-methoxycarbonyl)ethenyl-3-methoxycarbonyl-2,3-di-hydrobenzofuran (compound 9a or 9b) as a yellow oily substance.

In this case, the following two kinds of compounds 9a and 9b are obtained from the respective compound 8a and compound 8b.

Compound 9a

-continued

Compound 9b

It should be noted that, in FIG. 1, only the compound9a is depicted for convenience sake.

Next, the compound9a or 9b is dissolved in predetermined amounts of methanol (MeOH), tetrahydrofuran (THF) and distilled water. To the reaction solution is added a predetermined amount of lithium hydroxide-monohydrate (LiOH—H$_2$O), and the mixture is stirred at room temperature for a predetermined time period. The ration liquid is added to an aqueous solution of 10% citric acid, and subjected to extraction using ethyl acetate. The resultant organic phase is washed with saturated saline, dried using magnesium sulfate (MgSO$_4$) and then subjected to filtration. The filtrate is concentrated under reduced pressure using an evaporator, to thereby obtain an oily substance. The resultant oily substance is dissolved in dehydrated dichloromethane, to which boron trichloride (BCl$_3$) is added, and the mixture is stirred at −78° C. for a predetermined time period. Subsequently, the temperature is raised to 0° C. and the mixture is stirred for a predetermined time period. To the reaction liquid is added a predetermined amount of an aqueous solution of saturated sodium bicarbonate or 1M hydrochloric acid, and extraction is performed using predetermined amounts of ethyl acetate and an aqueous solution of saturated sodium bicarbonate or 1M hydrochloric acid. The resultant organic phase is washed with saturated saline, dried using magnesium sulfate (MgSO$_4$), and then subjected to filtration. The filtrate is concentrated under reduced pressure using an evaporator, to thereby obtain an oily substance. The resultant oily substance is subjected to purification using silica gel column chromatography, to thereby obtain 5-(2-carboxylethenyl)-2,3-dihydro-2-(4-hydroxyphenyl)-3-benzofurancarboxylic acid (compound 10a or 10b) as an oily substance.

In this case, from the compound9a (cis form), the following compound 10a (transform) is obtained.

Compound 10a

From the compound 9b (cis form), the following compound 10b (trans form) is obtained.

Compound 10b

To sum up, in the present reaction, the cis form is converted to the trans form. It should be noted that, in FIG. 1, only the compound 10a is depicted for convenience sake.

Next, the compound 10a or 10b is dissolved in a methanol solution, to which a small amount of concentrated sulfuric acid is added and the mixture is stirred. After stirring for a predetermined time period, to the reaction liquid is added an excess amount of sodium bicarbonate to terminate the reaction, and the mixture is subjected to extraction using predetermined amounts of ethyl acetate (AcOEt) and saturated saline. The aqueous phase is further subjected to extraction using a predetermined amount of ethyl acetate, which is repeated several times. The resultant organic phase is dried using magnesium sulfate (MgSO$_4$) and then subjected to filtration. The filtrate is concentrated under reduced pressure using an evaporator and dried in a desiccator, to thereby obtain methyl-5-(2-carboxyethenyl)-2,3-dihydro-2-(4-hydroxyphenyl)-3-benzofurancarboxylate (compound 11a or 11b) as an oily substance.

In this case, from the compound 10a, the following compound 11a is obtained.

Compound 11a

From the compound 10b, the following compound 11b is obtained.

Compound 11b

It should be noted that, in FIG. 1, only the compound 11a is depicted for convenience sake.

(3) Condensation of Base Moiety (Compound 17) and Acyl Moiety (Compound 11a or 11b)

To the compound 11a or 11b are added the compound 17, N-ethyl-N'-3-dimethylaminopropyl carbodiimide (WSCI), and 1-hydroxybenzotriazole (HOBt), and the mixture is stirred in dimethylformamide (DMF) at room temperature. To the reaction liquid is added saturated saline and the mixture is subjected to extraction using ethyl acetate. The organic phase is washed with saturated saline, dried using magnesium sulfate (MgSO$_4$), and then subjected to filtration. The filtrate is concentrated under reduced pressure using an evaporator, to thereby obtain an oily substance. The oily substance is subjected to purification using silica gel chromatography, concentrated under reduced pressure and dried in a desiccator, to thereby obtain methyl-5-(1E)-[[bis[[(1,1-dimethylethoxy)carbonyl]amino]methylene]amino]-3-oxo-1-propenyl]-2,3-dihydro-2-(4-hydroxyphenyl)-3-benzofurancarboxylate (compound 18a or 18b).

In this case, from the compound 11a, the following compound 18a is obtained.

liquid and the mixture is freeze-dried. The resultant substance is subjected to purification using high performance liquid chromatography (HPLC). The solvent is removed from the solution fraction using an evaporator under reduced pressure, and the resultant substance is freeze-dried. Subsequently, to the product is added hydrochloric acid, and the mixture is allowed to stand still at 5° C. for a predetermined time period and freeze-dried, to thereby obtain a compound 19a or 19b of the present invention as a pale yellow oily substance.

In this case, from the compound 18a, the following compound 19a is obtained.

Compound 18a

From the compound 11b, the following compound 18b is obtained.

Compound 18b

It should be noted that, in FIG. 1, only the compound 18a is depicted for convenience sake.

(4) Synthesis of methyl-5-(1E)-[[4-(aminoiminomethyl)amino]butylamino]-3-oxo-1-propenyl]-2,3-dihydro-2-(4-hydroxyphenyl)-3-benzofurancarboxylate) (Compound 19a or 19b) of the Present Invention To the compound 18a or 18b is added trifluoroacetic acid (TFA) and the mixture is stirred at room temperature. After a predetermined time period, water is added to the reaction Compound 19a From the compound 18b, the following compound 19b is obtained.

Compound 19b

It should be noted that, in FIG. 1, only the compound 19a is depicted for convenience sake.

(5) Synthesis of 5-(1E)-[[4-(aminoiminomethyl)amino]butylamino]-3-oxo-1-propenyl]-2,3-dihydro-2-(4-hydroxyphenyl)-3-benzofurancarboxylic acid) (compound 20a or 20b) of the Present Invention To the compound 18a or 18b is added trifluoroacetic acid (TFA) and the mixture is stirred at room temperature. Subsequently, purified water is added thereto and the mixture is freeze-dried. Trifluoroacetic acid (TFA) and 1N hydrochloric acid (trifluoroacetic acid:1N hydrochloric acid=1:2) are added thereto and the mixture is stirred at room temperature. After a predetermined time period, purified water is added thereto and the mixture is freeze-dried. 0.01N hydrochloric acid is added thereto and a fraction is obtained through high performance liquid chromatography (HPLC). The solvent is removed from the solution fraction using an evaporator under reduced pressure, and the resultant substance is freeze-dried, to thereby obtain a compound 20a or 20b of the present invention.

In this case, from the compound 18a, the following compound 20a is obtained.

It should be noted that, in FIG. 1, only the compound 20a is depicted for convenience sake.

As described above, in the synthesis of the compound of the present invention, when $Rh_2(R\text{-}PTTL)_4$ is used as the optically-active dirhodium (II) complex, the compound 19a or compound 20a is synthesized, and when $Rh_2(S\text{-}PTTL)_4$ is used as the optically-active dirhodium (II) complex, the compound 19b or compound 20b is synthesized.

2. $\alpha_1$ Adrenergic Receptor Antagonistic Agent

The $\alpha_1$ adrenergic receptor antagonistic agent of the present invention includes the compound 19 (at least one of the compound 19a and the compound 19b) or compound 20 (at least one of the compound 20a and the compound 20b) synthesized in the manner as described above as a raw material (active ingredient), and can be used as drugs as will be described below.

(Drug)

The $\alpha_1$ adrenergic receptor antagonistic agent of the present invention is applicable to treatments of various disorders whose development may involve the $\alpha_1$ adrenergic receptor, and is used as a drug (for example, antihypertensive drug, drug for prostatic hypertrophy and diuretic).

Examples of the disorder treatment include reducing risks of pheochromocytoma (hypertension control of a patient with pheochromocytoma, and remission of intestinal pseudo-ob- Compound 20a From the compound 18b, the following compound 20b is obtained.

struction), hypertension, primary systemic hypertension, newborn persistent pulmonary hypertension, and arterioscle- Compound 20b rosis; diminution of congestive heart failure and pulmonary congestion; treatment of a patient with vasospastic disorder, mitral valve insufficiency or aortic valve insufficiency; mitigation of urinary retention and nocturia caused by benign prostatic hypertrophy (BPH); reduction of urinary outflow resistance in a patient with prostatic obstruction or bladder outlet obstruction caused by isolation from a parasympathetic nerve center due to spinal cord injury, suppression of male sexual dysfunction and autonomic nerve hyperreflexia occurrence in a patient with transverse spinal cord injury; promotion of uterine contraction or alleviation from migraine immediately after delivery; and prevention of bleeding due to uterine atony after delivery.

Especially, the $\alpha_1$ adrenergic receptor antagonistic agent of the present invention is not only effective as an antihypertensive drug, and but also effective as a drug for prostatic hypertrophy, because of its diuretic effect.

Furthermore, the $\alpha_1$ adrenergic receptor antagonistic agent of the present invention can be used as a diuretic, and may be used not only for the purpose of enhancing an diuretic effect in a healthy individual, but also for the purpose of improving an ability to urinate which has been once lowered due to operation, aging, fatigue, disease, injury or the like.

If desired, taking the effect in the user (intaker) or convenience of the user (intaker) into account, the amount of the compound 19 or compound 20 in the drug can be adjusted when formulating. It is preferable that the dosage of compound 19 or compound 20 per day is 0.01 mg to 1,000 mg. It is preferable that the compound 19 or compound 20 be contained in an amount of approximately 0.01 mg/kg to 10 g/kg of a final product.

The drug may be formulated in various forms using the conventional formulation techniques, such as capsule, tablet, powder, granule, drinkable preparation, syrup, injectable and intravenous drip. Examples of additives to be used in the production include micro crystalline cellulose, lactose, cornstarch and magnesium stearate.

3. Composition

The composition of the present invention includes the compound 19 or compound 20 synthesized in the manner as described above, has an action through the $\alpha_1$ adrenergic receptor, and can be used as food and beverage, food and beverage additive and veterinary feedstuff, as will be described below.

With respect to the composition of the present invention, it is preferable that an amount of the compound 19 or compound 20 to be contained be approximately 0.01 mg/kg to 10 g/kg of a final product. In addition, taking the convenience of the user (intaker) into account, the composition may be provided in a form of individual package prepared so as to contain the compound 19 or compound 20 in a dosage amount of 0.01 mg to 1000 mg per day.

(Food and Beverage)

The food and beverage of the present invention (e.g., food and beverage, health food, food for special dietary use or the like) can be produced by conventional methods, using the compound 19 or compound 20 in combination with various food product materials and additives. Examples of the usable food product material include caramel, gelatin, granulated sugar, gum base, various seasonings, veterinary feedstuff, fruit juice, liquid sugar, coffee extract, fermented milk, powdered skim milk, alcoholic beverage, and purified water. Examples of the usable additive include citric acid, L-ascorbic acid, dietary salt, polyglycerol fatty acid ester, various aroma essences, powdered sorbitol, calcium carbonate, and lactose.

The food and beverage may be of any type and in any form, such as solid food, liquid food or nonessential grocery food. Examples include agricultural food products, such as bread, noodle, cooked rice, confectionery (e.g. biscuit, cake, candy, chocolate, Japanese confectionery, gummy candy and chewing gum), soybean curd and processed products thereof; seasonings, such as sweet cooking rice wine, vinegar, soy sauce, soybean paste and dressing; livestock food products, such as yogurt, ham, bacon, sausage, and mayonnaise; fish paste products such as steamed fish paste and pounded fish cake, beverages, such as fruit juice drink, cold beverage, sports drink, coffee beverage, tea drink, and carbonated beverage; and furthermore, powdered milk or dairy product, such as baby milk and milk for coffee.

Examples of other food and beverage include alcoholic beverage with an enhanced diuretic effect by adding the compound 19 or 20 to a malt-fermented beverage, such as beer, low-malt beer and low-alcohol malt-fermented beverage; and fermented liquors, such as wine, refined sake and medicinal liquor. Further examples include an alcoholic beverage with a diuretic effect, to be consumed as aperitif or food-accompanying alcohol, the effect being rendered by adding the compound 19 or 20 to a distilled spirit, such as whiskey, brandy and Shochu spirit.

The health food may be of any type and in any form, and examples include tablet, capsule, solid and liquid.

Examples of the food for special dietary use include food for frail health, milk powder for parturient and breast-feeding mother, infant modified milk powder, geriatric food, food with health claims (food with nutrient function claims, food for specified health use).

(Food and Beverage Additive)

The food and beverage additive of the present invention can be produced by mixing the compound 19 or compound 20 with, for example, commercially available seasoning, seasoned liquid, aroma essence, Furikake condiment, edible oil or soup stock.

The food and beverage additive of the present invention may be in a form of products for food and beverage with various purposes, and examples include seasoning, seasoned liquid, aroma essence, Furikake condiment, edible oil and soup stock. In addition, there can also be mentioned the food and beverage additive with an diuretic effect which contains the compound 19 or compound 20 as one of nutritional fortifier components.

(Veterinary Feedstuff)

The veterinary feedstuff of the present invention can be produced by mixing the compound 19 or compound 20 with, for example, commercially available veterinary feedstuff.

(Other Compositions)

Examples for other compositions include compositions containing processed wheat product (preferably processed barley product, processed malt product, processed malt radicle product, malt radicle extract and the like) with the compound 19 or compound 20 added thereto.

In addition, the above-mentioned composition may be accompanied with an indication with respect to a function based on an action through the $\alpha_1$ adrenergic receptor. It should be noted that the expression "indication with respect to a function" in the present invention means, for example, an indication stating that a specific health purpose is expected, an indication stating that the composition is for health application, or an indication regarding application, effect or efficacy.

EXAMPLES

The compound of the present invention will be described in more detail with reference to the following Examples and Experimental Examples. It should be noted that the compounds 19a, 19b, 20a and 20b of the present invention are synthesized through various intermediate bodies described in the following Examples. However, reagents to be used, amounts thereof, and reaction conditions are not limited to those described below, and as long as the reaction can proceeds, they can be arbitrarily set.

Example 1

Synthesis of 1-allyloxy-4-bromobenzene (Compound 2)

Under an atmosphere replaced with argon, p-bromophenol (compound 1) (5.00 g, 28.9 mmoL) and potassium carbonate (5.00 g, 36.18 mmoL, 1.252 eq) were stirred in dimethylformamide (10 mL), and to the mixture was added allyl bromide (2.8 mL, 31.8 mmoL, 1.100 eq), which was further stirred at room temperature overnight. The reaction liquid was subjected to extraction using 100 mL of water and 100 mL of diethyl ether, and an aqueous phase was further subjected to extraction using 50 mL of diethyl ether. Two organic phases were combined and dried using magnesium sulfate, and then subjected to filtration. The filtrate was concentrated under reduced pressure using an evaporator, to thereby obtain a pale yellow oily substance (6.27 g). The resultant oily substance was subjected to purification using silica gel chromatography (with a developer of n-hexane:ethyl acetate=100:1), to thereby obtain 1-allyloxy-4-bromobenzene (compound 2) (6.04 g, 28.5 mmoL, 98%) as a transparent and colorless oily substance.

With respect to the resultant 1-allyloxy-4-bromobenzene (compound 2), nuclear magnetic resonance spectrum analysis ($^1$H-NMR) was performed, the result of which is as follows:

$^1$H-NMR (500 MHz, CDCl$_3$) δH: 7.36 (2H, dt, J=10 Hz and 2.5 Hz, Ar—H), 6.79 (2H, dt, J=10 Hz and 2.5 Hz, Ar—H), 6.02 (1H, m, CH$_2$—CH=CH$_2$), 5.40 (1H, dq, J=20 Hz and 3 Hz, CH=CH—H), 5.29 (1H, dq, J=10 Hz and 3 Hz, CH=CH—H), 4.50 (2H, dt, J=5 Hz and 1.6 Hz, O—CH$_2$—CH)

Example 2

Synthesis of 2-allyl-4-bromophenol (Compound 3)

Under an atmosphere replaced with argon, 1-allyloxy-4-bromobenzene (compound 2) (6.04 g, 28.5 mmoL) was heated in an oil bath at 200° C. for 3 hours. The reaction liquid was subjected to extraction using 100 mL of water and 100 mL of diethyl ether, and an aqueous phase was further subjected to extraction using 50 mL of diethyl ether. Two organic phases were combined, dried using magnesium sulfate, and then subjected to filtration. The filtrate was concentrated under reduced pressure using an evaporator, to thereby obtain a black oily substance. The resultant oily substance was subjected to purification using silica gel chromatography (with a developer of n-hexane:ethyl acetate=95:5), to thereby obtain 2-allyl-4-bromophenol (compound 3) (5.20 g, 24.43 mmoL, 86%) as a pale yellow oily substance.

With respect to the resultant 2-allyl-4-bromophenol (compound 3), nuclear magnetic resonance spectrum analysis ($^1$H-NMR) was performed, the result of which is as follows:

$^1$H-NMR (500 MHz, CDCl$_3$) δH: 7.25-7.23 (2H, m, Ar—H), 6.69 (1H, m, Ar—H), 5.97 (1H, m, CH$_2$—CH=CH$_2$), 5.19 (1H, m, CH=CH—H), 5.17 (1H, m, CH=CH—H), 5.02 (s, Ar—OH), 3.36 (2H, d, J=5 Hz, Ar—CH$_2$—CH)

Example 3

Synthesis of 2-allyl-1-(4-benzyloxy-benzyloxy)-4-bromobenzene (Compound 4)

Under an atmosphere replaced with argon, 2-allyl-4-bromophenol (compound 3), potassium carbonate and benzyloxy-benzylchloride (BnBr) were dissolved in dimethylformamide (DMF), and stirred at room temperature for 3 hours.

After confirming that the starting materials were disappeared using thin-layer chromatography (TLC) (with a developer of n-hexane:ethyl acetate=4:1), the reaction liquid was subjected to extraction using 20 mL of water and 20 mL of ethyl acetate. The organic phase was washed with 20 mL of water twice, dried using magnesium sulfate, and then subjected to filtration. The filtrate was concentrated under reduced pressure using an evaporator. The resultant residue was subjected to purification using silica gel flash chromatography (silica gel flash c.c.) (with a developer of n-hexane:ethyl acetate×4:1), to thereby obtain 2-allyl-1-(4-benzyloxy-benzyloxy)-4-bromobenzene (compound 4) as light brown solid.

Example 4

Synthesis of 2-(4-benzyloxy-benzyloxy)-5-bromophenylacetic acid (Compound 5)

2-allyl-1-(4-benzyloxy-benzyloxy)-4-bromobenzene (compound 4) (200 mg, 0.489 mmoL), sodium periodate (633 mg, 2.95 mmoL, 6.023 eq), and ruthenium (III) chloride trihydrate (4.4 mg, 0.0168 mmoL, 0.034 eq) were stirred in carbon tetrachloride ($CCl_4$)-acetonitrile (MeCN)-water (2:2:3, 3.5 mL) for 15 hours, to which sodium periodate (209.2 mg, 0.978 mmoL, 2.00 eq) was added and the mixture was stirred for another 3 hours. The reaction liquid was subjected to extraction using 30 mL of water and 30 mL chloroform, and an aqueous phase was washed with 30 mL of chloroform twice. Two organic phases were combined and dried using magnesium sulfate, and then concentrated under reduced pressure using an evaporator. The resultant oily substance was subjected to purification using silica gel chromatography (with a developer of n-hexane:ethyl acetate=9:1-->4:1-->3:1), to thereby obtain 2-(4-benzyloxy-benzyloxy)-5-bromophenylacetic acid (compound 5) (83 mg, 0.194 mmoL, 40%) as white solid.

With respect to the resultant 2-(4-benzyloxy-benzyloxy)-5-bromophenylacetic acid (compound 5), nuclear magnetic resonance spectrum analysis ($^1$H-NMR) was performed, the result of which is as follows:

$^1$H-NMR (500 MHz, $CDCl_3$) δH: 7.28-7.42 (10H, m, Ar—H), 6.94 (1H, d, Ar—H), 6.79 (1H, d, Ar—H), 5.04 (2H, s, O—$CH_2$—Ar), 4.96 (2H, 5, O—$CH_2$—Ar), 3.64 (2H, s, Ar—CH—COO)

Example 5

Synthesis of 2-(4-benzyloxy-benzyloxy)-5-bromophenylacetic acid methyl ester (Compound 6)

To 2-(4-benzyloxy-benzyloxy)-5-bromophenylacetic acid (compound 5) (40 mg, 0.0937 mmoL) was added diazomethane ($CH_2N_2$) prepared in an ether solution, and the mixture was stirred at room temperature, and 40 minutes later, the solvent was volatilized. The resultant substance was subjected to purification using silica gel chromatography (with a developer of n-hexane:ethyl acetate=99:1-->98:2-->96:4), to thereby obtain 2-(4-benzyloxy-benzyloxy)-5-bromophenylacetic acid methyl ester (compound 6) (31.1 mg, 0.0704 mmoL, 75%) as white powder.

With respect to the resultant 2-(4-benzyloxy-benzyloxy)-5-bromophenylacetic acid methyl ester (compound 6), nuclear magnetic resonance spectrum analysis ($^1$H-NMR) was performed, the result of which is as follows:

$^1$H-NMR (500 MHz, $CDCl_3$) δH: 7.28-7.44 (10H, m, Ar—H), 6.97 (1H, d, Ar—H), 6.79 (1H, d, Ar—H), 5.07 (2H, s, O—$CH_2$—Ar), 4.97 (2H, s, O—$CH_2$—Ar), 3.61 (3H, s, O—$CH_3$), 3.60 (2H, s, Ar—$CH_2$—CO)

Example 6

Synthesis of 2-(4-benzyloxy-benzyloxy)-5-bromophenyl-diazo-acetic acid methyl ester (Compound 7)

-continued

7

2-(4-benzyloxy-benzyloxy)-5-bromophenylacetic acid methyl ester (compound 6) (200 mg, 0.453 mmoL) and p-acetamidebenzenesulfonyl azide (compound 21) (157 mg, 0.654 mmoL, 1.443 eq) were stirred in 6 mL of acetonitrile (MeCN), during which 1,8-diazabicyclo[5.4.0]undec-7-ene (DBU) (200 μl, 1.34 mmoL, 2.952 eq) was added thereto. Two hours later, to the mixture was added 6 mL of an aqueous solution of saturated ammonium chloride, and extraction was performed using 20 mL of diethyl ether and 16 mL of an aqueous solution of saturated ammonium chloride. The organic phase was washed with 10 mL of saturated saline, dried using magnesium sulfate, and subjected to filtration. The filtrate was concentrated under reduced pressure using an evaporator, to thereby obtain an oily substance. The resultant oily substance was subjected to purification using silica gel chromatography (with a developer of n-hexane:ethyl acetate=94:6), and further subjected to purification using spherical neutral silica gel chromatography (with a developer of n-hexane:ethyl acetate=94:6), to thereby obtain 2-(4-benzyloxy-benzyloxy)-5-bromophenyl-diazo-acetic acid methyl ester (compound 7) (90 mg, 0.193 mmoL, 42.5%) as a yellow oily substance.

With respect to the resultant 2-(4-benzyloxy-benzyloxy)-5-bromophenyl-diazo-acetic acid methyl ester (compound 7), nuclear magnetic resonance spectrum analysis ($^1$H-NMR) was performed, the result of which is as follows:

$^1$H-NMR (500 MHz, CDCl$_3$) δH: 7.73 (1H, s, Ar—H), 7.28-7.44 (8H, m, Ar—H), 6.99 (2H, d, Ar—H), 6.83 (1H, d, Ar—H), 5.07 (2H, s, O—CH$_2$—Ar), 4.99 (2H, s, O—CH$_2$—Ar), 3.82 (3H, s, O—CH$_3$)

Example 7

Synthesis of 5-bromo-2-(4-benzyloxy)phenyl-3-methoxycarbonyl-2,3-di-hydrobenzofuran (Compound 8a or 8b)

Under an atmosphere replaced with argon, 2-(4-benzyloxy-benzyloxy)-5-bromophenyl-diazo-acetic acid methyl ester (compound 7) (25 mg, 0.0535 mmoL), Rh$_2$(R-PTTL)$_4$ (6 mg, 0.00422 mmoL, 0.0788 eq), and a molecular sieve of 4 Å (20 mg) were added to distilled dichloromethane (1.3 mL), and stirred at −78° C. for 30 minutes. The reaction liquid was concentrated under reduced pressure using an evaporator. The residue was subjected to purification using silica gel chromatography (with a developer of n-hexane:ethyl acetate=1:1), to thereby obtain 5-bromo-2-(4-benzyloxy) phenyl-3-methoxycarbonyl-2,3-di-hydrobenzofuran (compound 8a or 8b) (8.7 mg, 0.0186 mmoL, 37%) as a white powdery substance.

With respect to the resultant 5-bromo-2-(4-benzyloxy) phenyl-3-methoxycarbonyl-2,3-di-hydrobenzofuran (compound 8a or 8b), nuclear magnetic resonance spectrum analysis ($^1$H-NMR) was performed, the result of which is as follows:

$^1$H-NMR (500 MHz, CDCl$_3$) δH: 7.22-7.40 (9H, m, Ar—H), 6.92 (2H, d, Ar—H), 6.81 (1H, d, Ar—H), 5.95 (1H, d, O—CH—Ar), 5.05 (2H, s, O—CH$_2$—Ar), 4.56 (1H, d, CH—CO$_2$-Me), 3.24 (3H, s, CO$_2$CH$_3$)

Example 8

Synthesis of 2-(4-benzyloxy)phenyl-5-trans(2-methoxycarbonyl)ethenyl-3-methoxycarbonyl-2,3-di-hydrobenzofuran (Compound 9a or 9b)

9a

Under an atmosphere replaced with argon, 5-bromo-2-(4-benzyloxy)phenyl-3-methoxycarbonyl-2,3-di-hydrobenzofuran (compound8a or 8b) (20 mg, 0.0457 mmoL), methyl acrylate (compound 22) (25 mL, 0.276 mmoL, 6.037 eq), tri(o-tolyl)phosphine (2.8 mg, 0.00920 mmoL, 0.201 eq), palladium acetate (Pd(OAc)$_2$) (0.6 mg, 0.00267 mmoL, 0.0585 eq) and distilled triethylamine (NEt$_3$) (4.5 μL, 0.0456 mmoL, 0.998 eq) were reacted in dehydrated dimethylformamide (DMF) for 24 hours in a sealed container, which was in an oil bath at 100° C. After the reaction container was cooled, the reaction liquid was added to 1 mL of an aqueous solution of saturated ammonium chloride and 1 mL of ethyl acetate in a 50 mL-eggplant-shaped flask, which had been cooled to 0° C. in advance. Extraction was performed using 30 mL of an aqueous solution of saturated ammonium chloride and 30 mL of ethyl acetate, and the organic phase was washed with 30 mL of an aqueous solution of saturated ammonium chloride three times. The organic phase was dried using magnesium sulfate, and then subjected to filtration. The filtrate was concentrated under reduced pressure using an evaporator, to thereby obtain an oily substance. The resultant oily substance was subjected to purification using silica gel chromatography (with a developer of n-hexane:ethyl acetate=95:5, 9:1, 4:1), to thereby obtain 2-(4-benzyloxy)phenyl-5-trans(2-methoxycarbonyl)ethenyl-3-methoxycarbonyl-2,3-di-hydrobenzofuran (compound9a or 9b) (8 mg, 0.0180 mmoL, 39.4%) as a yellow oily substance.

With respect to the resultant 2-(4-benzyloxy)phenyl-5-trans(2-methoxycarbonyl)ethenyl-3-methoxycarbonyl-2,3-di-hydrobenzofuran (compound9a and 9b), nuclear magnetic resonance spectrum analysis ($^1$H-NMR) was performed, the result of which is as follows:

$^1$H-NMR (500 MHz, CDCl$_3$) δH: 7.65 (1H, d, Ar-olefin-H), 7.55 (1H, s, Ar—H), 7.42-7.30 (8H, m, Ar—H), 6.97 (2H, d, Ar—H), 6.88 (1H, d, Ar—H), 6.32 (1H, d, CO-olefin-H), 6.10 (1H, d, O—CH—Ar), 5.06 (2H, s, O—CH$_2$—Ar), 4.28 (1H, d, CH—CO$_2$-Me), 3.83 (3H, s, CO$_2$CH$_3$), 3.79 (3H, S, CO$_2$CH$_3$)

Example 9

Synthesis of 5-(2-carboxylethenyl)-2,3-dihydro-2-(4-hydroxyphenyl)-3-benzofurancarboxylic acid (Compound 10a or 10b)

2-(4-benzyloxy)phenyl-5-trans(2-methoxycarbonyl)ethenyl-3-methoxycarbonyl-2,3-di-hydrobenzofuran (compound9aor 9b) (12 mg, 0.027 mmoL) was dissolved in 1 mL of methanol (MeOH), 200 mL of tetrahydrofuran (THF) and 20 mL of distilled water. To the reaction solution was added a predetermined amount of lithium hydroxide-monohydrate (LiOH—H$_2$O), and the mixture was stirred at room temperature for 2 hours. The reaction liquid was added to an aqueous solution of 10% citric acid, and subjected to extraction using ethyl acetate. The resultant organic phase was washed with saturated saline twice, dried using magnesium sulfate (MgSO$_4$), and then subjected to filtration. The filtrate was concentrated under reduced pressure using an evaporator, to thereby obtain an oily substance. The resultant oily substance was dissolved in 1 mL of dehydrated dichloromethane, to which boron trichloride (BCl$_3$) was added, and the mixture was stirred at −78° C. for 30 minutes. Subsequently, the temperature was raised to 0° C. and the mixture was stirred for 90 minutes. To the reaction liquid was added 10 mL of 1M hydrochloric acid, and extraction was performed using 20 mL of ethyl acetate and 10 mL of 1M hydrochloric acid. The resultant organic phase was washed with 20 mL of saturated saline twice, dried using magnesium sulfate (MgSO$_4$), and then subjected to filtration. The filtrate was concentrated under reduced pressure using an evaporator, to thereby obtain an oily substance. The resultant oily substance was subjected to purification using silica gel column chromatography (solvent: CHCl$_3$:MeOH:AcOH=9:1:0.2), to thereby obtain 4.8 mg (0.0147 mmoL, 54.4%) of 5-(2-carboxylethenyl)-2,3-dihydro-2-(4-hydroxyphenyl)-3-benzofurancarboxylic acid (compound 10a or 10b) as an oily substance.

With respect to the resultant 5-(2-carboxylethenyl)-2,3-dihydro-2-(4-hydroxyphenyl)-3-benzofurancarboxylic acid (compound 10a or 10b), nuclear magnetic resonance spectrum analyses ($^1$H-NMR and $^{13}$C-NMR) was performed, the results of which are as follows:

$^1$H-NMR (CD$_3$OD) δ 4.25 (1H, d, 7.5 Hz), 5.96 (1H, d, 7.5 Hz), 6.32 (1H, d, 15.8 Hz), 6.77 (2H, d, 8.3 Hz), 6.86 (1H, d, 8.3 Hz), 7.19 (2H, d, 8.3 Hz), 7.48 (1H, d, 8.3 Hz), 7.63 (1H, d, 15.8 Hz), 7.64 (1H, s)

$^{13}$C-NMR (CD$_3$OD) δ 54.95, 87.08, 109.65, 115.13, 115.19, 115.50, 124.89, 126.14, 126.97, 127.12, 127.74, 130.53, 131.18, 145.05, 157.57, 161.36, 169.51, 172.53

Example 10

Synthesis of methyl-5-(2-carboxyethenyl)-2,3-dihydro-2-(4-hydroxyphenyl)-3-benzofurancarboxylate (Compound 11a or 11b)

10a

MeOH | H$_2$SO$_4$

11a 5-(2-carboxylethenyl)-2,3-dihydro-2-(4-hydroxyphenyl)-3-benzofurancarboxylic acid (compound 10a or 10b) (32.8 mg, 0.106 mmoL) was dissolved in 2 mL of a methanol solution immediately after distillation, to which two drops of concentrated sulfuric acid were added and the mixture was stirred. After stirring for 90 minutes, to the reaction liquid was added an excess amount of sodium bicarbonate to terminate the reaction, and the mixture was subjected to extraction using 30 mL of ethyl acetate (AcOEt) and 30 mL of saturated saline. The aqueous phase was further subjected to extraction using 30 mL of ethyl acetate, which was repeated three times. The resultant organic phase was dried using magnesium sulfate (MgSO$_4$) and then subjected to filtration. The filtrate was concentrated under reduced pressure using an evaporator and dried in a desiccator, to thereby obtain 40.7 mg of methyl-5-(2-carboxyethenyl)-2,3-dihydro-2-(4-hydroxyphenyl)-3-benzofurancarboxylate (compound 11a or 11b) as a yellow oily substance. Purification of the thus obtained oily substance was not performed and the procedure was advanced to the next reaction.

Example 11

Synthesis of methyl-5-(1E)-[[bis[[(1,1-dimethylethoxy)carbonyl]amino]methylene]amino]-3-oxo-1-propenyl]-2,3-dihydro-2-(4-hydroxyphenyl)-3-benzofurancarboxylate (Compound 18a or 18b)

11a

WSCl
HOBt
DMF

17

18a

To methyl-5-(2-carboxyethenyl)-2,3-dihydro-2-(4-hydroxyphenyl)-3-benzofurancarboxylate (compound 11a or 11b) (36.4 mg) were added N,N'-di-Boc-agmatine (compound 17) (70.7 mg, 0.214 mmoL, 2.00 eq), N-ethyl-N'-3-dimethylaminopropyl carbodiimide (WSCI) (41.0 mg, 0.214 mmoL, 2.00 eq), and 1-hydroxybenzotriazole (HOBt) (28.9 mg, 0.214 mmoL, 2.00 eq), and the mixture was stirred in 3 mL of dimethylformamide at room temperature. Progress of the reaction was confirmed using high performance liquid chromatography (column: J'sphere ODS-H80, 4.5 mm (inner diameter)×250 mm (length), measurement wavelength: 280 nm, flow rate: 0.5 mL/min, elute: methanol:water:trifluoroacetic acid=80:20:0.1), and the mixture was stirred overnight. To the reaction liquid was added 30 mL of saturated saline and the mixture was subjected to extraction using 30 mL of ethyl acetate. The organic phase was washed with 30 mL of saturated saline three times, dried using magnesium sulfate, and then subjected to filtration. The filtrate was concentrated under reduced pressure using an evaporator, to thereby obtain an oily substance. The oily substance was subjected to purification using silica gel chromatography [silica gel 60N (sphere, neutral) 63 µm to 210 µm, 1.4 cm (inner diameter)× 20 cm (length), elute (hexane:ethyl acetate=1:4)], and each fraction was analyzed using thin-layer chromatography (with a developer of hexane:ethyl acetate=1:4). The fraction containing the target was concentrated under reduced pressure and dried in a desiccator. As a result, 35.4 mg (53.9%, 2 steps) of methyl-5-(1E)-[[bis[[(1,1-dimethylethoxy)carbonyl]amino]methylene]amino]-3-oxo-1-propenyl]-2,3-dihydro-2-(4-hydroxyphenyl)-3-benzofurancarboxylate (compound 18a or 18b) was obtained.

With respect to the resultant compounds 18a and 18b, nuclear magnetic resonance spectrum analyses ($^1$H-NMR and $^{13}$C-NMR) and mass spectral analysis (FAB-MS) were performed, the results of which are as follows:

$^1$H-NMR (500 MHz, DMSO-$d_6$) δH: 11.48 (1H, s), 9.57 (1H, s), 8.28 (1H, t, J=5.73 Hz), 8.01 (1H, t, J=5.73 Hz), 7.51 (1H, s), 7.40 (1H, d, J=6.87 Hz), 7.38 (1H, d, J=16.04 Hz), 7.18 (2H, d, J=8.59 Hz), 6.87 (1H, d, J=8.59 Hz), 6.73 (2H, d, J=8.59), 6.45 (1H, d, J=16.04 Hz), 5.88 (1H, d, J=7.45 Hz), 4.43 (1H, d, J=7.45 Hz), 3.71 (3H, s), 3.26 (2H, m), 3.14 (2H, m), 1.48-1.34 (22H, m)

$^{13}$C-NMR (500 MHz, DMSO-$d_6$) δ: 171.4, 165.6, 163.7, 160.3, 158.3, 155.8, 152.6, 138.7, 130.7, 130.3, 128.7, 128.3, 126.1, 124.5, 120.4, 115.9, 110.3, 86.9, 83.4, 78.7, 54.4, 53.2, 28.5, 28.1, 27.0, 26.7

FAB-MS: 653 (MH$^+$), HRMS (FAB): 653.3181 (MH$^+$), Exact MS 653.3187 ($C_{34}H_{45}O_9N_4$, MH$^+$)

Example 12

Synthesis of methyl-5-(1E)-[[4-(aminoiminomethyl)amino]butylamino]-3-oxo-1-propenyl]-2,3-dihydro-2-(4-hydroxyphenyl)-3-benzofurancarboxylate (compound 19a or 19b)

To the compound 18a or 18b (35.4 mg) was added 100% trifluoroacetic acid (TFA) (2 mL) and the mixture was stirred at room temperature. Thirty minutes later, water was added to the reaction liquid and the mixture was freeze-dried. The resultant substance was subjected to purification using high performance liquid chromatography (column: COSMOSIL 5C$_{18}$-AR-II, 10 mm (inner diameter)×250 mm (length), measurement wavelength: 280 nm, flow rate: 3.0 mL/min, elute: acetonitrile:water:trifluoroacetic acid=30:70:0.1). Acetonitrile was removed from the solution fraction using an evaporator under reduced pressure, and the resultant substance was freeze-dried. Subsequently, to the product was added 4 mL of 0.01N hydrochloric acid, and the mixture was allowed to stand still at 5° C. for 30 minutes and freeze-dried. As a result, methyl-5-(1 E)-[[4-(aminoiminomethyl)amino]butylamino]-3-oxo-1-propenyl]-2,3-dihydr o-2-(4-hydroxyphenyl)-3-benzofurancarboxylate (compound 19a or 19b) (22.3 mg: 90.9%) was obtained as a pale yellow oily substance. The yield of the compound 19a or 19b from the compound 11a or 11b was 49.0%.

With respect to the resultant methyl-5-(1E)-[[4-(aminoiminomethyl)amino]butylamino]-3-oxo-1-propenyl]-2,3-dihydr o-2-(4-hydroxyphenyl)-3-benzofurancarboxylate (compound 19a and 19b), nuclear magnetic resonance spectrum analyses ($^1$H-NMR and $^{13}$C-NMR) and mass spectral analysis (FAB-MS) were performed, the results of which are as follows:

$^1$H-NMR (500 MHz, DMSO-d$_6$) δH: 9.64 (1H, s), 8.16 (1H, t, J=5.73 Hz), 7.75 (1H, t, J=5.73 Hz), 7.51 (1H, s), 7.41 (1H, d, J=8.02 Hz), 7.34 (1H, d, J=15.46 Hz), 7.18 (2H, d, J=8.59 Hz), 6.87 (1H, d, J=8.02 Hz), 6.75 (2H, d, J=8.02), 6.50 (1H, d, J=16.04 Hz), 5.88 (1H, d, J=7.45 Hz), 4.44 (1H, d, J=7.45 Hz), 3.71 (3H, s), 3.14 (2H, m), 3.09 (2H, m), 1.45 (4H, br-s)

$^{13}$C-NMR (500 MHz, DMSO-d$_6$) δ: 171.4, 165.8, 160.3, 158.3, 157.4, 138.7, 130.7, 130.2, 128.7, 128.3, 126.1, 124.5, 120.3, 115.9, 110.4, 86.9, 54.4, 53.2, 41.0, 38.8, 26.9, 26.6

FAB-MS: 453 (MH$^+$), HRMS (FAB): 453.2135 (MH$^+$), Exact MS 453.2138 (C$_{24}$H$_{29}$O$_5$N$_4$, MH$^+$)

Example 13

Synthesis of 5-(1E)-[[4-(aminoiminomethyl)amino]butylamino]-3-oxo-1-propenyl]-2,3-dihydro-2-(4-hydroxyphenyl)-3-benzofurancarboxylic acid (Compound 20a or 20b)

To the compound 18a or 18b (12.6 mg, 0.0193 mmoL) was added trifluoroacetic acid (TFA) (1 mL) and the mixture was stirred at room temperature for 30 minutes. Subsequently, purified water was added thereto and the mixture was freeze-dried. Trifluoroacetic acid (0.5 mL) and 1N hydrochloric acid (1 mL) were added thereto and the mixture was stirred at room temperature. Progress of the reaction was confirmed using high performance liquid chromatography (column: J'sphere ODS-H80, 4.6 mm (inner diameter)×250 mm (length), measurement wavelength: 280 nm, flow rate: 0.5 mL/min, elute: acetonitrile:water:trifluoroacetic acid=30:70: 0.1). After 24 hours, purified water was added thereto and the mixture was freeze-dried. 1.3 mL of 0.01N hydrochloric acid was added thereto and a fraction was obtained through high performance liquid chromatography (column: YMC-Pack ODS-A, 20 mm (inner diameter)×250 mm (length), measurement wavelength: 280 nm, flow rate: 6.0 mL/min, elute: acetonitrile:water:trifluoroacetic acid=30:70:0.1). Acetonitrile was removed from the solution fraction using an evaporator under reduced pressure, and the resultant substance was freeze-dried. As a result, 3.2 mg (0.00730 mmoL, 37.8%) of 5-(1E)-[[4-(aminoiminomethyl)amino]butylamino]-3-oxo-1-propenyl]-2,3-dihydro-2-(4-hydroxyphenyl)-3-benzofurancarboxylic acid (compound 20a or 20b) was obtained as the largest peak (retention time (Rt)=22 minutes).

Experimental Example 1

α₁ Adrenergic Receptor Binding Test

The compound 19a synthesized in Examples above was weighed, to which 100% dimethylsulfoxide (DMSO) was added so as to prepare a solution at 10-fold of the final concentration. The solution was diluted with an assay buffer, to thereby prepare four types of specimens with different concentrations (0.02 µM, 0.2 µM, 2 µM, 20 µM). In addition, with respect to each of the compound 19b, the racemic mixture of the compounds 19a and 19b, and the racemic mixture of the compounds 20a and 20b, likewise, four types of specimens were prepared (see Mitchel, A. D. et al., (1989) Brt. J. Pharmacol., 98: 883-889).

Next, as the $\alpha_1$ adrenergic receptor, an $\alpha_{1A}$ receptor (one of subtypes of the $\alpha_1$ adrenergic receptor) was used, and a binding ability to the $\alpha_{1A}$ receptor was examined.

It has been known that the $\alpha_{1A}$ receptors are present on a membrane of a rat salivary gland. To an assay buffer (250 µL) containing a membrane homogenate of a rat salivary gland (150 µg in terms of protein amount) were added the above-mentioned specimen and [³H]prazosin (0.06 nM) as ligand, to thereby prepare a reaction liquid, which was then incubated at 22° C. for 60 minutes. After the incubation, the reaction liquid was subjected to suction filtration using a glass fiber filter (GF/B, manufactured by Packard) which had been washed with 0.3% PEI (polyethyleneimine), to terminate reaction. The glass fiber filter was washed with 50 mM Tris-HCl cooled with ice, washing being repeated several times. The glass fiber filter was dried, a scintillation cocktail (Microscint 0, manufactured by Packard) was added thereto, and residual radioactivity on the filter was measured using a liquid scintillation counter (Topcount, manufactured by Packard). An amount of specific binding of [³H]prazosin was obtained by subtracting an amount of non-specific binding in the presence of phentolamine (10 µM) from a total binding amount of [³H]prazosin.

Figure 2:
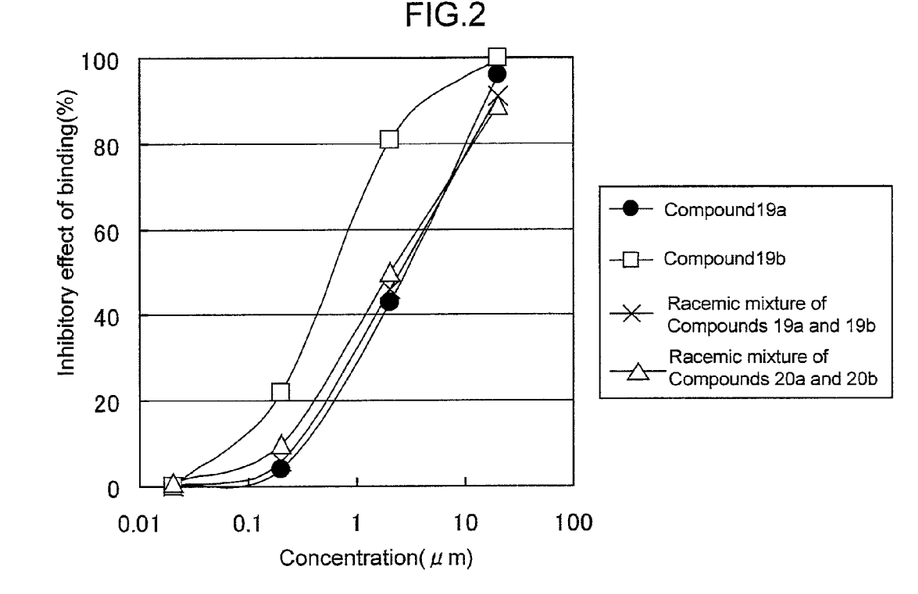
FIG. 2 is a graph showing results of $\alpha_1$ adrenergic receptor binding test of the compound of the present invention.

The results of the $\alpha_1$ adrenergic receptor binding test are shown in FIG. 2. As is apparent from the results in the drawing, it was confirmed that each of the compound 19a and the compound 20 has a dosage-dependency, and IC₅₀ values were 2.03 µM for the compound 19a, 0.61 µM for the compound 19b, 2.39 µM for the racemic mixture of the compounds 19a and 19b, and 1.99 µM for the racemic mixture of the compounds 20a and 20b.

Accordingly, it was elucidated that each of the compound 19a, the compound 19b, the racemic mixture of the compounds 19a and 19b, and the racemic mixture of the compounds 20a and 20b has a strong binding ability to the $\alpha_{1A}$ receptor.

Experimental Example 2

Rat Tail Artery Constriction Inhibition Test

The compound 9a, the compound 19b, the racemic mixture of the compounds 19a and 19b, and the racemic mixture of the compounds 20a and 20b synthesized in Examples above were evaluated with respect to the function as the $\alpha_1$ adrenergic receptor antagonist.

Since the $\alpha_1$ adrenergic receptor antagonist has been known to have a vasoconstriction inhibition effect, the constriction inhibition effect of the compounds was examined using rat tail artery.

1. Preparation of Sample Solution

The compound 19a synthesized in Examples above was weighed, to which 100% dimethylsulfoxide (DMSO) was added so as to prepare a sample solution (stock solution) (concentration of the compound 19a: 100 mM). In addition, the compound 19b, the racemic mixture of the compounds 19a and 19b, and the racemic mixture of the compounds 20a and 20b were prepared likewise.

2. Rat Tail Artery Constriction Inhibition Test

A tissue (rat tail artery) with an exposed endothelium was suspended in an organ bath filled with 20 mL of saline (NaCl: 118.0 mM, KCl: 4.7 mM, MgSO₄: 1.2 mM, CaCl₂: 2.5 mM, NaHCO₃: 25 mM, glucose: 11.0 mM) (pH7.4) at 37° C., into which 95% oxygen/5% carbon dioxide had been fed. In the rat tail artery tissue, the $\alpha_2$ adrenergic receptor, β adrenergic receptor, histamine H1 receptor, muscarine receptor, and 5-HT2 receptor had been expressed like the $\alpha_1$ adrenergic receptor had, and in order to block the actions of these receptors, antagonistic agents (antagonists) for the respective receptor, i.e., yohimbine (1 µM), propranol (1 µM), pyrilamine (1 µM), atropine (1 µM), and methysergide (1 µM), were added.

In order to measure the contraction of the tissue caused by an action of the $\alpha_1$ adrenergic receptor, the tissue was connected to a force transducer which outputs a tension of the tissue as data. The tension in a static state was adjusted to become 1 g, and was maintained for 60 minutes (during that time period, the tissue was repeatedly washed with saline to readjust the tension). To the tissue was added 10 µM of a reference agonist (phenylephrine 1.0E-05M), and it was confirmed that the tissue responded in a normal manner. At the same time, there was recorded the tension (g) obtained by the contraction of the tissue caused by the action of the reference agonist. After confirming that the tissue responded in a normal manner, the reference agonist was washed out once, and the tissue was allowed to stand still for up to 15 minutes until the response returns to a static state (tension: 1 g).

After the response returned to the static state (tension: 1 g), the reference agonist was added so that the contraction rate of the tissue becomes 100%.

Next, the sample solution or a diluted solution thereof was added in such a manner that each of the concentrations of the compound 19a, the compound 19b, the racemic mixture of the compounds 19a and 19b, and the racemic mixture of the compounds 20a and 20b in the organ bath was increased in three stages (1 µM, 10 µM, 100 µM). Every time the concentration was increased, the tension was measured, and the contraction rate was calculated using the following equation. It should be noted that, every time the sample solution was added, the resultant mixture was allowed to stand still for up to 15 minutes until the response becomes stable.

Contraction rate (%)=(tension (g) upon adding the sample solution−1)/(tension (g) upon adding the reference agonist−1)×100

When the contraction rate (%) was decreased in a concentration-dependent manner, the corresponding compound 19a, compound 19b, racemic mixture of the compounds 19a and 19b, or racemic mixture of the compounds 20a and 20b, were considered to have the $\alpha_1$ adrenergic receptor antagonistic agent (antagonist) effect (see Docherty, J. R. et al. (1981) Naunyn Schemiedeberg's Arch. Pharmacol., 317: 5-7).

Figure 3:
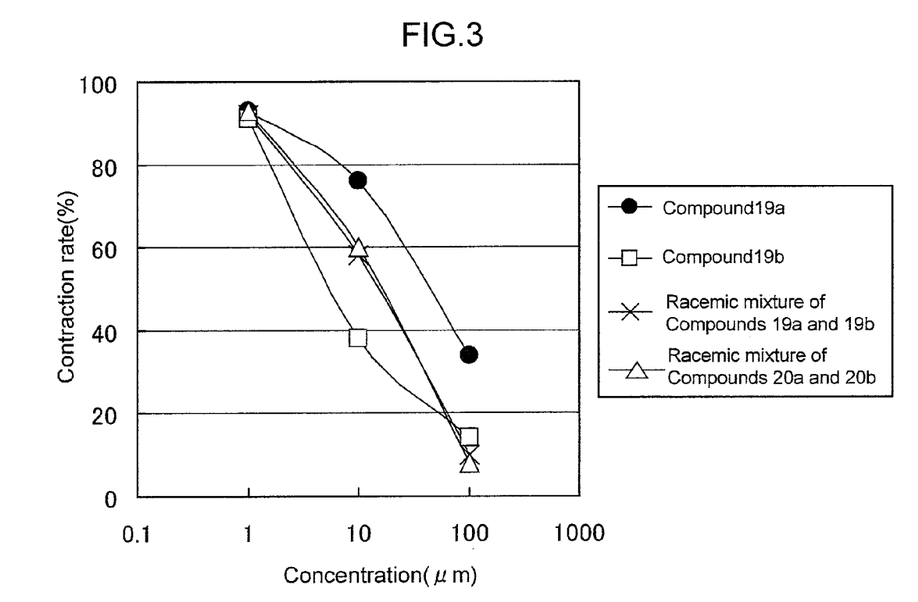
FIG. 3 is a graph showing results of rat tail artery constriction test of the compound of the present invention.

The results of the rat tail artery constriction test are shown in FIG. 3. Each of the compound 19a, the compound 19b, the racemic mixture of the compounds 19a and 19b, and the racemic mixture of the compounds 20a and 20b suppressed a response in the reference agonist (phenylephrine) in a dosage-dependent manner (rat tail artery was relaxed).

As shown above, it is confirmed that each of the compound 19a, the compound 19b, the racemic mixture of the compounds 19a and 19b, and the racemic mixture of the com- pounds 20a and 20b has an strong antagonistic action, and for example, has a vasodilatory effect and a diuretic effect associated therewith.

INDUSTRIAL APPLICABILITY

The present invention can be used as drug (e.g. antihypertensive drug, drug for prostatic hypertrophy, and diuretic), food and beverage, food and beverage additive, veterinary feedstuff and the like.

The invention claimed is:

1. A compound represented by the following formula (1):

2. A compound represented by the following formula (2):

3. A composition which comprises a compound represented by the following formula (1):

4. A composition which comprises a compound represented by the following formula (2):

5. The composition according to claim 3, which is any one of food and beverage, food and beverage additive, and veterinary feedstuff.

6. The composition according to claim 4, which is any one of food and beverage, food and beverage additive, and veterinary feedstuff.

* * * * *